United States Patent [19]
Jako

[11] Patent Number: 5,813,978
[45] Date of Patent: *Sep. 29, 1998

[54] METHOD AND APPARATUS FOR DIRECT ACCESS ENDOSCOPIC SURGERY

[75] Inventor: Geza J. Jako, Melrose, Mass.

[73] Assignee: Atlantis Surgical, Inc., Princeton, N.J.

[*] Notice: The term of this patent shall not extend beyond the expiration date of Pat. No. 5,503,617.

[21] Appl. No.: 622,555

[22] Filed: Mar. 25, 1996

Related U.S. Application Data

[63] Continuation of Ser. No. 277,094, Jul. 19, 1994, Pat. No. 5,503,617.

[51] Int. Cl.⁶ .................................................. A61B 17/02
[52] U.S. Cl. ............................................................ 600/201
[58] Field of Search ..................... 600/201, 204, 600/208, 210, 213, 219, 221, 222, 223, 226, 227, 228, 231, 233, 234, 245

[56] References Cited

U.S. PATENT DOCUMENTS

| | | |
|---|---|---|
| 891,091 | 6/1908 | Mouthuy . |
| 943,263 | 12/1909 | Moraweck . |
| 1,275,520 | 8/1918 | Bell . |
| 2,669,993 | 2/1954 | Curutchet . |
| 2,670,732 | 3/1954 | Nelson .................................. 600/234 |
| 2,693,795 | 11/1954 | Grieshaber . |
| 3,724,449 | 4/1973 | Gauthier .......................... 600/234 X |
| 4,048,987 | 9/1977 | Hurson .............................. 600/233 X |
| 4,122,844 | 10/1978 | Rabban . |
| 4,263,899 | 4/1981 | Burgin . |
| 4,562,832 | 1/1986 | Wilder et al. . |
| 4,627,421 | 12/1986 | Symbas et al. . |
| 4,852,552 | 8/1989 | Chaux . |
| 5,035,232 | 7/1991 | Lutze et al. . |
| 5,195,505 | 3/1993 | Josefsen . |
| 5,234,460 | 8/1993 | Stouder, Jr. ............................ 606/205 |
| 5,503,617 | 4/1996 | Jako ..................................... 600/201 |

FOREIGN PATENT DOCUMENTS

| | | | |
|---|---|---|---|
| 547292 | 3/1932 | Germany ............................. 600/222 |

*Primary Examiner*—Jeffrey A. Smith
*Attorney, Agent, or Firm*—Heslin & Rothenberg, P.C.

[57] ABSTRACT

A retractor endoscope for less invasive, direct access endoscopic surgery includes a rigid frame capable of supporting applied loads required to perform retraction of an incision site. The rigid frame includes a handle at one end and a lower blade mount rotatably connected to the opposite end. A translation frame is slidably connected to the rigid frame and includes an upper blade mount rotatably connected thereto. Lower and upper blades are removably mounted to the lower and upper blade mounts respectively, with at least one of the blades including pivot mounts for high intensity fiberoptics. The angle of the lower blade along the lower blade mount rotatable connection and the angle of the upper blade along the upper blade mount rotatable connection are independently adjustable. The size of an operating window is determined by the distance between the lower and upper blade mounts and the angles of the lower and upper blades. A method of less invasive, direct access open surgery includes using the retractor with a tool having an angled handle.

48 Claims, 14 Drawing Sheets

METHOD AND APPARATUS FOR DIRECT ACCESS ENDOSCOPIC SURGERY

This application is a continuation of application Ser. No. 08/277,094 (now U.S. Pat. No. 5,503,617), filed Jul. 19, 1994.

The present invention relates in general to endoscopes and retractors for use in surgery.

It is the aim of such devices to provide access to and/or lighted viewing of a body cavity for the purpose of investigating and treating disorders.

It is an important object of this invention to provide an apparatus and techniques for a new concept in surgery, i.e. less invasive, direct access endoscopic surgery.

It is another object of the invention to create an operating window at the appropriate surgical site.

It is another object of the invention to provide new and improved instruments and techniques for performing precision procedures at a surgical site while using a retractor endoscope according to the invention.

Retractor endoscopes of the current invention utilize considerably shorter (e.g., 3–6 times shorter) incisions than conventional surgery and enable three-dimensional direct viewing of and direct access to the surgical site.

According to the invention, an apparatus for less invasive, direct access endoscopic surgery through an operating window comprises a rigid frame capable of supporting applied loads required to perform retraction of an incision site. The rigid frame includes a handle at one end having a handle slot therein, a lower blade mount rotatably connected to the opposite end, and rigid frame slots on either side of the rigid frame. A translation frame is slidably connected to the rigid frame through the handle slot and the rigid frame slots and includes an upper blade mount rotatably connected thereto.

The slidable connection is constructed and arranged to allow the handle to translate the translation frame with respect to the rigid frame to adjust the distance between the lower blade mount and the upper blade mount. The handle is constructed and arranged to prevent sliding of the translation frame along the slidable connection in at least one direction.

The apparatus further includes lower and upper blades each with free and supported ends mounted to the lower and upper blade mounts respectively. At least one of the lower and upper blades include a pivot mount for high intensity fiberoptics. A first adjusting screw and bar assembly is functionally connected between the lower blade mount and the rigid frame for independently adjusting the angle of the lower blade along the lower blade mount rotatable connection, and a second adjusting screw and bar assembly is functionally connected between the upper blade mount and the rigid frame for independently adjusting the angle of the upper blade along the upper blade mount rotatable connection. The first and second adjusting screw and bar assemblies are constructed and arranged to prevent rotation along the rotatable connections in at least one direction.

The size of the operating window between the lower and upper blades is determined by the distance between the lower blade mount and the upper blade mount set by the handle and the angles of the lower and upper blades set by the first and second adjusting screw and bar assemblies respectively.

According to one aspect of the invention, the lower and upper blades are removably mounted to the lower and upper blade mounts respectively.

According to another aspect of the invention, a scale is fixedly attached to the rigid frame for measuring the distance between the lower blade mount and the upper blade mount. In an exemplary embodiment of the invention, the scale is laser etched to the rigid frame.

According to another aspect of the invention, the lower blade and the upper blade differ in shape.

According to another aspect of the invention, the mechanism for translating the handle comprises a rack and pinion mechanism, a lead screw mechanism, or a ratchet mechanism. In an exemplary embodiment of the invention, a torque wrench is removably connected to the lead screw mechanism for increasing the applied torque.

According to another aspect of the invention, the apparatus further includes an adjustable microcamera mount slidably and rotatably connected to the rigid frame in one of the rigid frame slots and includes a cam lock for locking the mount in the rigid frame slot. The microcamera mount further includes a microcamera holder, the magnification of the microcamera being adjustable by sliding the microcamera within the microcamera holder when seated in the microcamera holder.

According to another aspect of the invention, the apparatus further includes a retention device, e.g., a sleeve or one or two slide blades, for keeping body parts clear of the operating window.

According to another aspect of the invention, the apparatus is formed from nonmagnetic material, e.g., titanium.

According to another aspect of the invention, a tool for performing medical procedures comprises a distal working portion including two working members, a proximal handle angled at a predetermined angle with respect to the distal working portion and including two finger rings, and a region between the distal working portion and the proximal handle including a single pivot joint.

The single pivot joint is constructed and arranged so that actuation of the proximal handle by moving the finger rings apart or together in substantially a horizontal plane results in the working members moving apart or together in a working plane tilted at the predetermined angle from the horizontal plane.

According to another aspect of the invention, the region between the distal working portion and the proximal handle further includes a gripping zone, e.g., knurled finger grips or a knurled finger pad, and a spike finger support integral with one of the finger rings. According to an exemplary embodiment of the invention, the tool is formed from nonmagnetic material, e.g., titanium.

According to another aspect of the invention, the predetermined angle is located proximal of the pivot joint and the distance between the proximal end of the handle and the angle location is less than the distance between the distal end of the working portion and the angle location.

According to another aspect of the invention, a hand retractor for retracting an incision comprises a blade, and a handle removably mounted to the blade. The blade includes pivot mounts for high intensity fiberoptics. The hand retractor is formed from a nonmagnetic material, e.g., titanium.

According to another aspect of the invention, a method of less invasive, direct access endoscopic surgery through an operating window is performed with an apparatus having a rigid frame capable of supporting applied loads required to perform retraction of an incision site. The rigid frame includes a handle at one end having a handle slot therein, a lower blade mount rotatably connected to the opposite end, and rigid frame slots on either side of the rigid frame. A translation frame is slidably connected to the rigid frame through the handle slot and the rigid frame slots and includes an upper blade mount rotatably connected thereto.

The slidable connection is constructed and arranged to allow the handle to translate the translation frame with respect to the rigid frame to adjust the distance between the lower blade mount and the upper blade mount. The handle is constructed and arranged to prevent sliding of the translation frame along the slidable connection in at least one direction.

The apparatus further includes lower and upper blades each with free and supported ends mounted to the lower and upper blade mounts respectively. At least one of the lower and upper blades include a pivot mount for high intensity fiberoptics. A first adjusting screw and bar assembly is functionally connected between the lower blade mount and the rigid frame for independently adjusting the angle of the lower blade along the lower blade mount rotatable connection, and a second adjusting screw and bar assembly is functionally connected between the upper blade mount and the rigid frame for independently adjusting the angle of the upper blade along the upper blade mount rotatable connection. The first and second adjusting screw and bar assemblies are constructed and arranged to prevent rotation along the rotatable connections in at least one direction.

The size of the operating window between the lower and upper blades is determined by the distance between the lower blade mount and the upper blade mount set by the handle and the angles of the lower and upper blades set by the first and second adjusting screw and bar assemblies respectively.

The method includes creating a small incision in the skin corresponding to a surgical site, retracting the incision by placing the apparatus with the lower and upper blades angled such that the free ends of the lower and upper blades are close together into the incision and adjusting the handle and the first and second adjusting screw and bar assemblies to create the desired sized operating window, illuminating the operating window with high intensity fiberoptic lighting, and performing surgery. According to an exemplary embodiment of the invention, the method further includes tilting the apparatus to adjust the operating window.

According to another aspect of the invention, the method further includes a manipulating tool having an angled handle so that the handle is clear of the operating window to enable visualization of the operating window during use of the tool.

The manipulating includes causing a working portion of the tool to enter the surgical site through the operating window while the angled handle remains removed from the surgical site, and performing surgery including manipulating the working portion of the tool through actuation of the angled handle while observing the surgical site through the operating window. The tool is selected from the group consisting of clamps, forceps, and needle holders.

In another aspect of the invention, the method further includes preretracting the incision with a hand retractor comprising a handle removably mounted to a first blade including pivot mounts for high intensity fiberoptics, removing the handle while inserting the apparatus, the apparatus including only one of the lower and upper blades leaving one of the lower and upper blade mounts empty, attaching the first blade to the apparatus in the empty blade mount during the insertion, and retracting the incision.

According to another aspect of the invention, a method of less invasive, direct access endoscopic surgery is performed with a retractor endoscope and a tool. The retractor endoscope includes adjustable blades that can be positioned to create an operating window. The tool includes a distal working portion comprising two working members, a proximal handle angled at a predetermined angle with respect to the distal working portion and including two finger rings, and a region between the distal working portion and the proximal handle including a single pivot joint. The single pivot joint is constructed and arranged so that actuation of the proximal handle by moving the finger rings apart or together in substantially a horizontal plane results in the working members moving apart or together in a working plane tilted at the predetermined angle from the horizontal plane. The angled handle enables visualization of an operating window during use of the tool.

The method includes creating a short incision in the skin corresponding to a surgical site, retracting the incision with the retractor endoscope, illuminating the operating window with high intensity fiberoptic lighting, causing a working portion of the tool to enter the surgical site through the operating window while the angled handle remains removed from the surgical site, and performing surgery including manipulating the working portion of the tool through actuation of the angled handle while observing the surgical site through the operating window.

Numerous other features, objects and advantages of the invention will become apparent from the following specification when read in connection with the accompanying drawings in which:

FIG. 9a is a side view of the microcamera mount.

Figure 1:
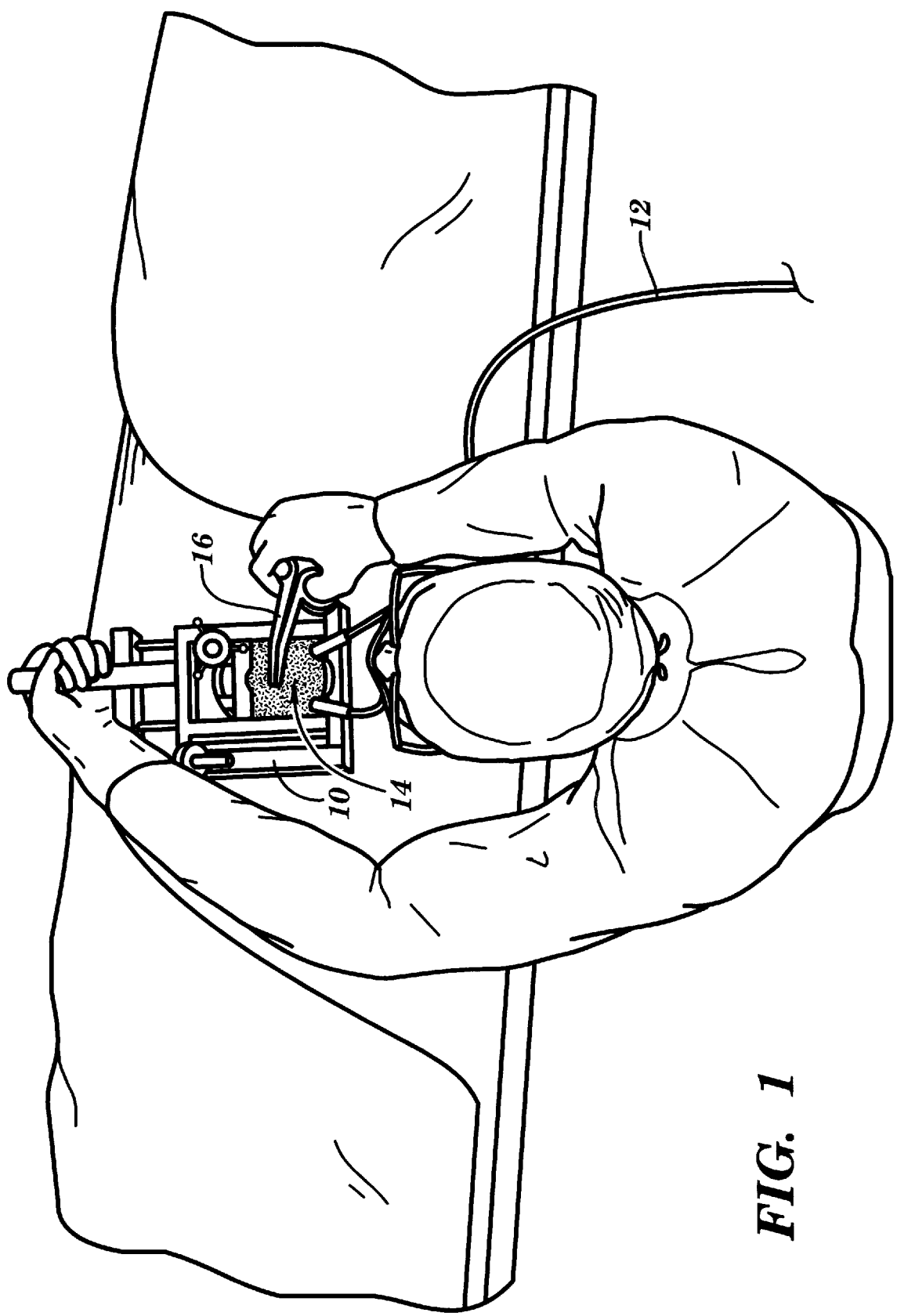
FIG. 1 is a diagrammatic representation of a surgical procedure utilizing the retractor endoscope of the invention.

With reference now to the drawings and more particularly FIG. 1 thereof, there is shown the retractor endoscope of the current invention in a patient during surgery. After incision, an opening is seen made by retractor endoscope 10 creating an operating window 14. Tool 16 for performing a surgical procedure is positioned at a surgical site through operating window 14. Illumination is provided by high intensity fiberoptic lighting 12. Utilizing retractor endoscope 10, a large operating window 14 can be created from an incision that is considerably shorter (e.g., 3–6 times shorter) than an incision which would be used in conventional open surgery to perform the same procedure.

Figure 2A:
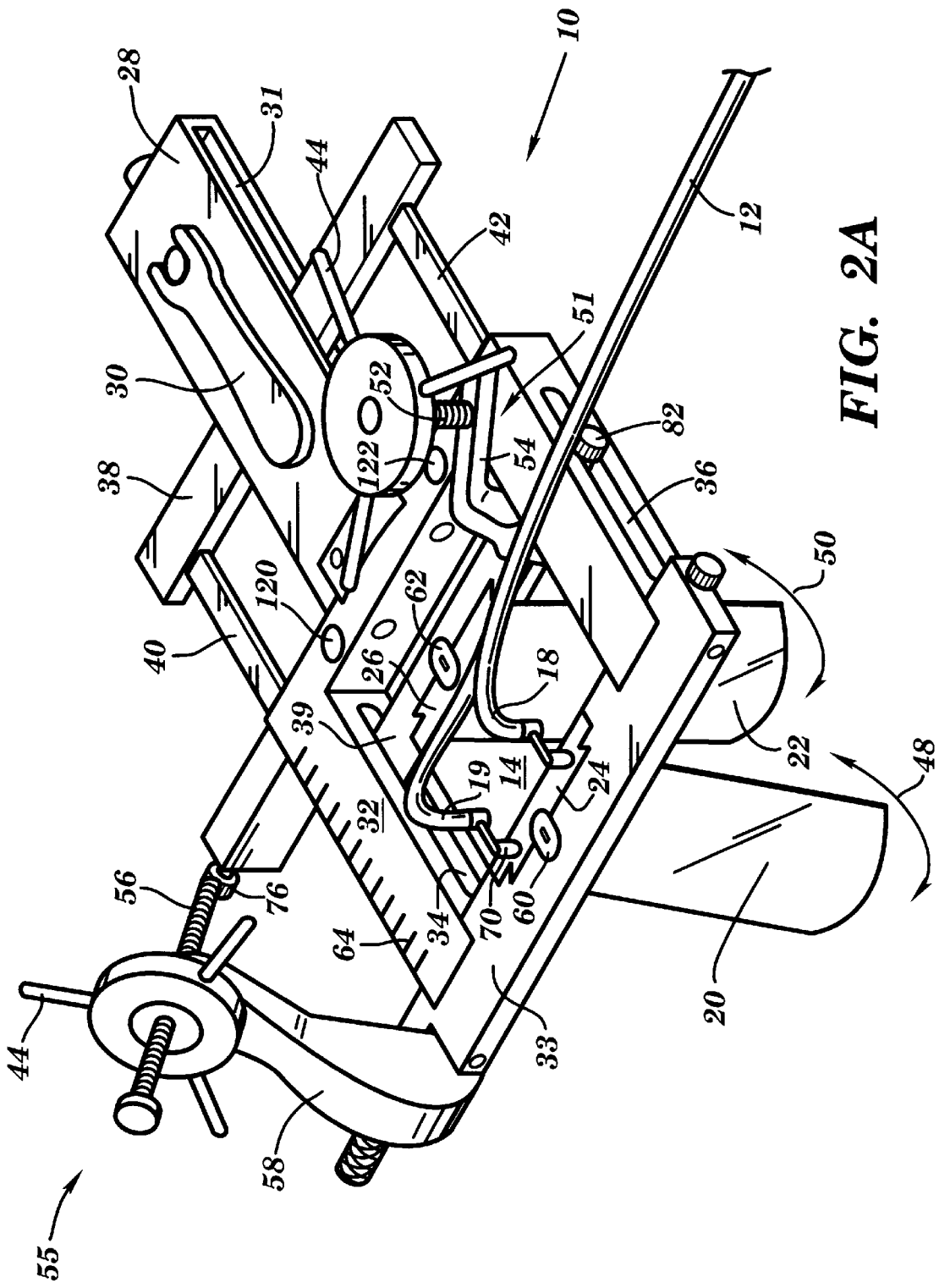
FIG. 2a is an exploded top view of the apparatus.

Referring to FIGS. 2 and 2A, retractor endoscope 10 for minimally invasive, direct access endoscopic surgery includes a very sturdy, rigid U-frame 32 capable of supporting applied loads required to perform retraction of incision sites. Rigid U-frame 32 includes a handle 28 at one end and a lower blade mount 33 rotatably connected to the opposite end. A translation frame 38 is slidably connected to rigid frame 32 through a handle slot 31 and rigid frame slots 34, 36. Translation frame 38 includes a rack 84 at one end and an upper blade mount 39 rotatably connected at the other end.

The slidable connection between translation frame 38 and rigid frame 32 enables handle 28 to translate frame 38 with respect to rigid frame 32, as described below. This translation adjusts the distance between lower blade mount 33 and upper blade mount 39. The slidable connection is constructed to prevent sliding in at least one direction to hold the position set by the user.

Retractor endoscope 10 includes lower and upper blades 20, 22 that are removably mounted to lower and upper blade mounts 33, 39 respectfully. Blades 20, 22 are slipped into angulated dovetail locks 24, 26 in blade mounts 33, 39. Angulated dovetail locks 24, 26 are angled, e.g., at 5 degrees, to set the position of the blades within the blade mounts preventing the blades from sliding through the blade mounts, and locking screws 60, 62 lock the blades in place.

At least one of blades 20, 22 includes pivot mounts 70 threadably attached to the blade for receiving high intensity fiberoptic lighting 12. Fiberoptic lighting 12 is a bifurcated bundle terminating in curved ends 18, 19, e.g., 90° bend, to insure that fiberoptic lighting 12 does not block the view of operating window 14 and does not interfere with the performance of the surgical procedure. For additional illumination, fiberoptic lighting 12 may be mounted to both blades.

A first adjusting screw and bar assembly 55 is functionally connected between lower blade mount 33 and rigid frame 32 for independently adjusting the angle of lower blade 20 along arrow 48 and a second adjusting screw and bar assembly 51 is functionally connected between upper blade mount 39 and rigid frame 32 for independently adjusting the angle of upper blade 22 along arrow 50. First and second assemblies 55, 51 are capable of preventing rotation along the rotatable connections in at least one direction in order to hold a set angle. Specifically, adjustment of angle 50 is accomplished by turning fine-threaded, e.g., ¼–28, high torque angle-adjusting screw 52 which adjusts lever arm 54 moving upper blade 22 along angle 50.

In a similar manner, angle 48 of lower blade 20 is adjusted by turning angle-adjusting screw 56, which adjusts lever arm 58 moving lower blade 20 along angle 48 (angle-adjusting screw 56 may have coarser threading, e.g., ¼–20, than angle-adjusting screw 52 due to a greater mechanical advantage gained by lever arm 58 being longer than lever arm 54). Heads of angle-adjusting screws 52, 56 may include pins 44 to aid in applying large torque to the threads. The capability of independently adjusting the distances between the proximal and distal ends of blades 20, 22 enable the user to expose a surgical site that is larger than operating window 14 thus requiring a shorter incision and less retraction of the incision than would conventionally be required to gain access to the same sized surgical site.

The size of operating window 14 between lower and upper blades 20, 22 is determined by the distance between lower blade mount 33 and upper blade mount 39 set by handle 29 and the angles; of lower and upper blades 20, 22 set by first and second assemblies 55, 51 respectfully. To enable a quick determination of the distance between lower and upper blade mounts 33, 39, main frame 32 includes a scale 64. Scale 64 is mounted to or formed on main frame 32 by any suitable method, e.g., laser etching.

Figure 10:
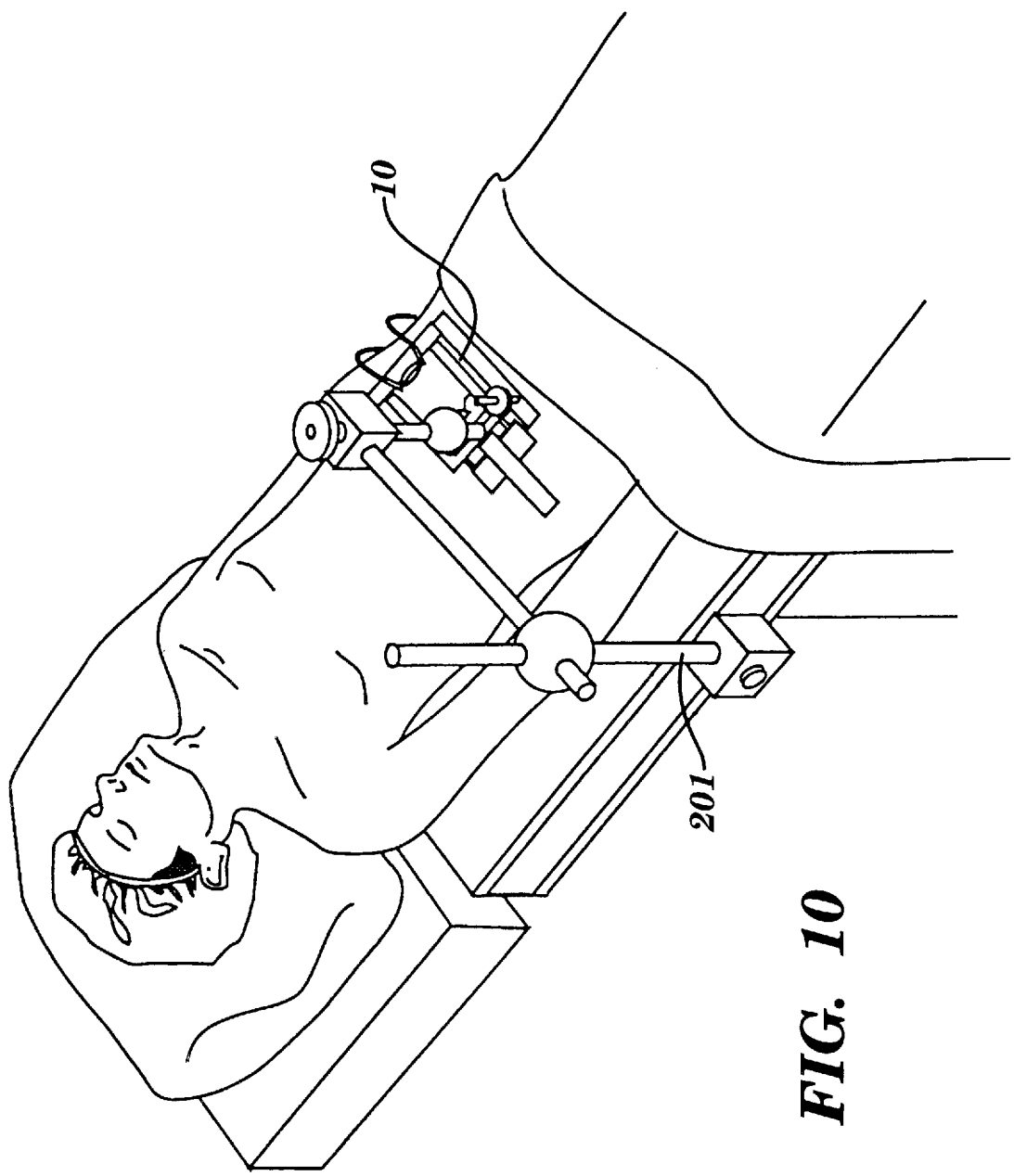
FIG. 10 is a diagrammatic representation of the retractor endoscope attached to an operating table by a securing arm.

Retractor endoscope 10 may be hand held by the surgeon during retraction of an incision site. Once operating window 14 has been created, retractor endoscope 10 need not be held by the surgeon during performance of a surgical procedure. If desired, retractor endoscope 10 may be attached to the operating table via mounting to a securing arm 201 (FIG. 10) at fixation sites 120, 122.

Referring to FIG. 2a, lower blade mount 33 is rotatably connected to rigid frame 32 via pins 72, 74. Spring loaded set screws 73, 75 hold pins 72, 74 in place and allow lower blade mount 33 to be quickly disconnected from rigid frame 32 to facilitate cleaning. Arm 58 is fixedly attached to lower blade mount 33 by screw 77. Angle-adjusting screw 56 is rotatably connected to rigid frame 32 by screw 76. Upper blade mount 39 is rotatably connected to translation frame 38 via screws 80, 82; side rods 40, 42 of translation frame 38 threadably receive screws 80, 82 respectively and upper blade mount 39 is clearance fit to screws 80, 82 to allow rotation. Arm 54 is fixedly attached to upper blade mount 39.

Figure 2B:
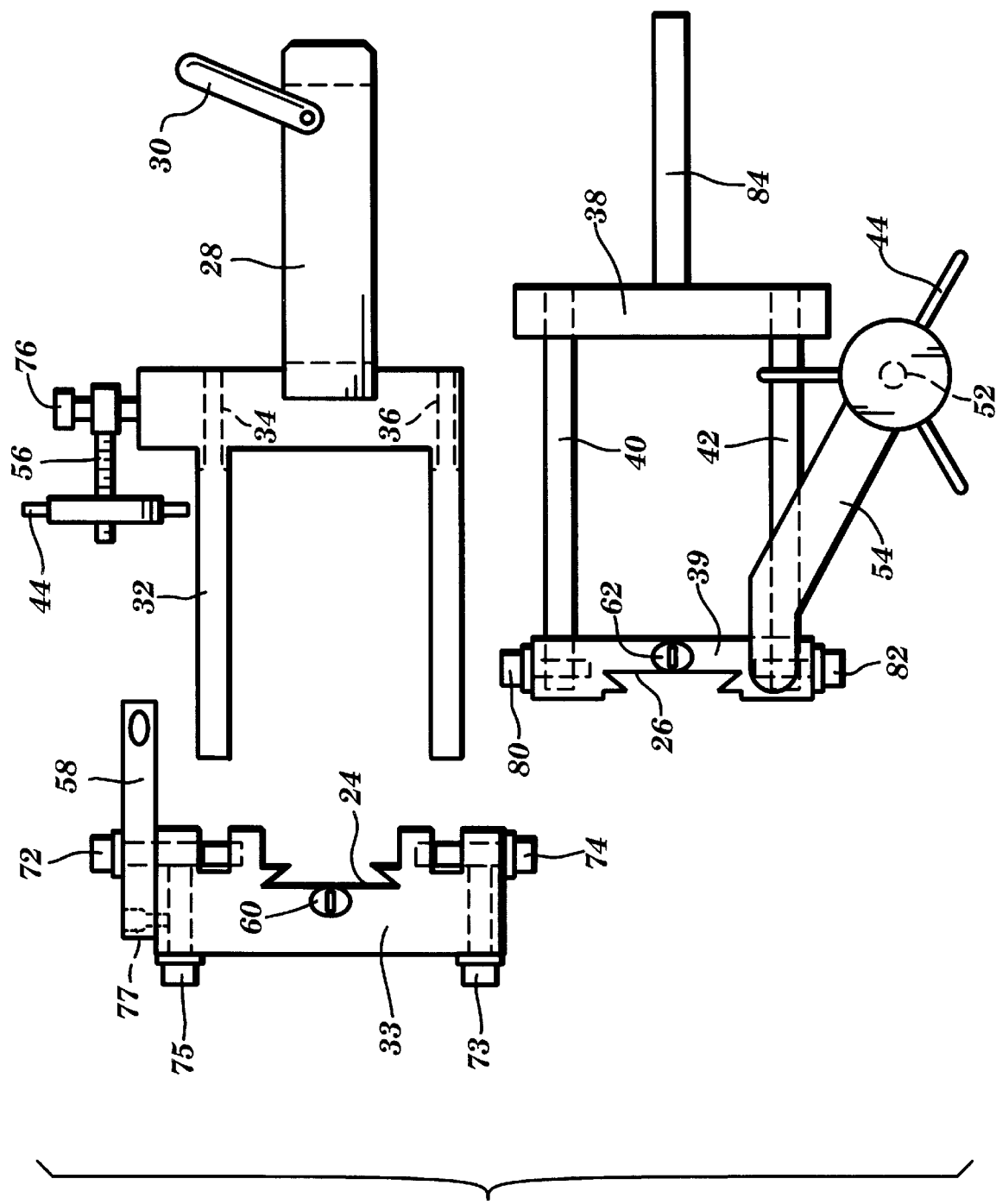
FIG. 2b is a side view of a handle of the apparatus.

Referring to FIG. 2b, one example of a mechanism for adjusting the distance between lower blade mount 33 and upper blade mount 39 is a type of rack and pinion system in which rotation of a rod 30 turns a pinion 86 which translates rack 84 along arrow 29 resulting in translation of frame 38.

Figure 2C:
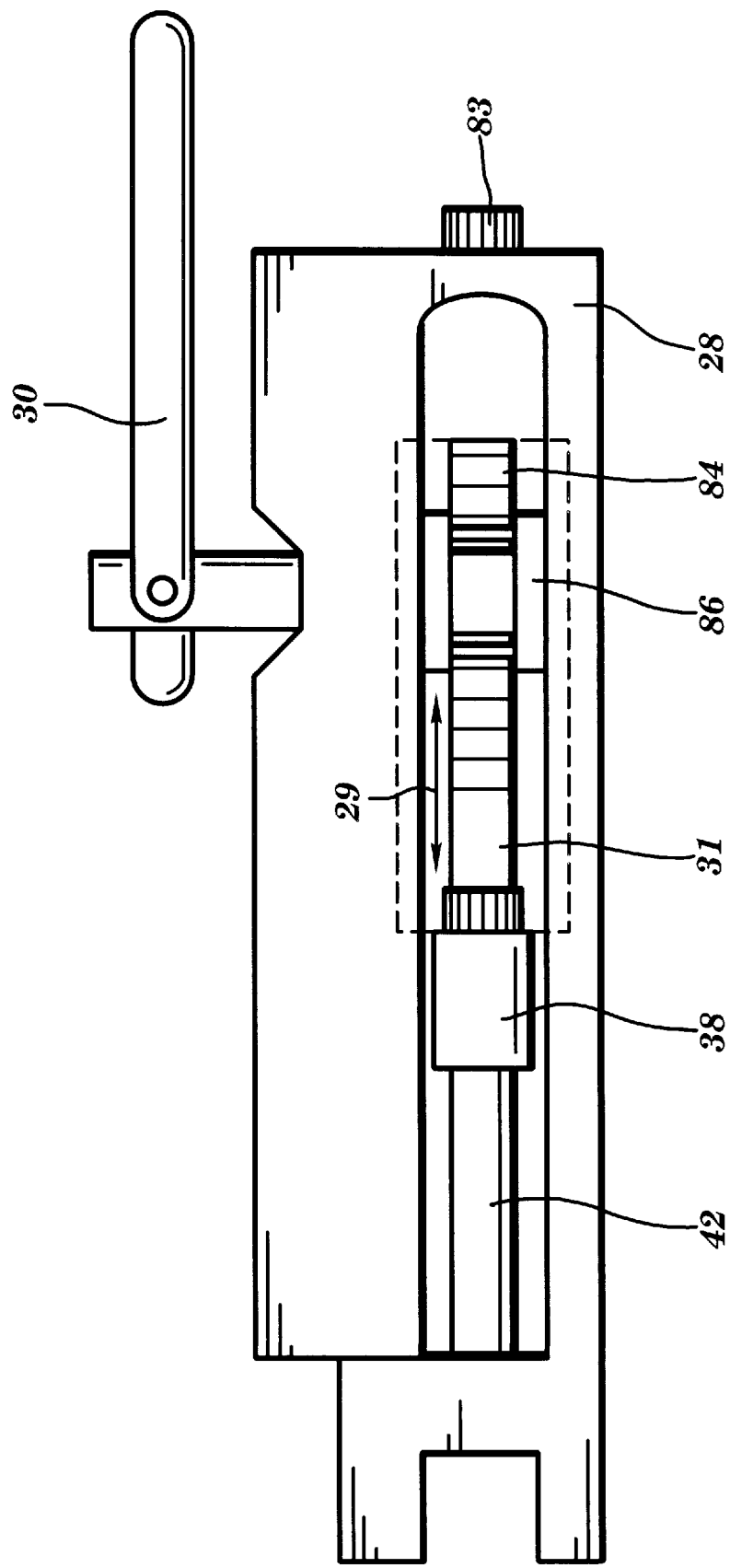
FIG. 2c is an exploded side view of the handle section of the apparatus.
Figure 2D:
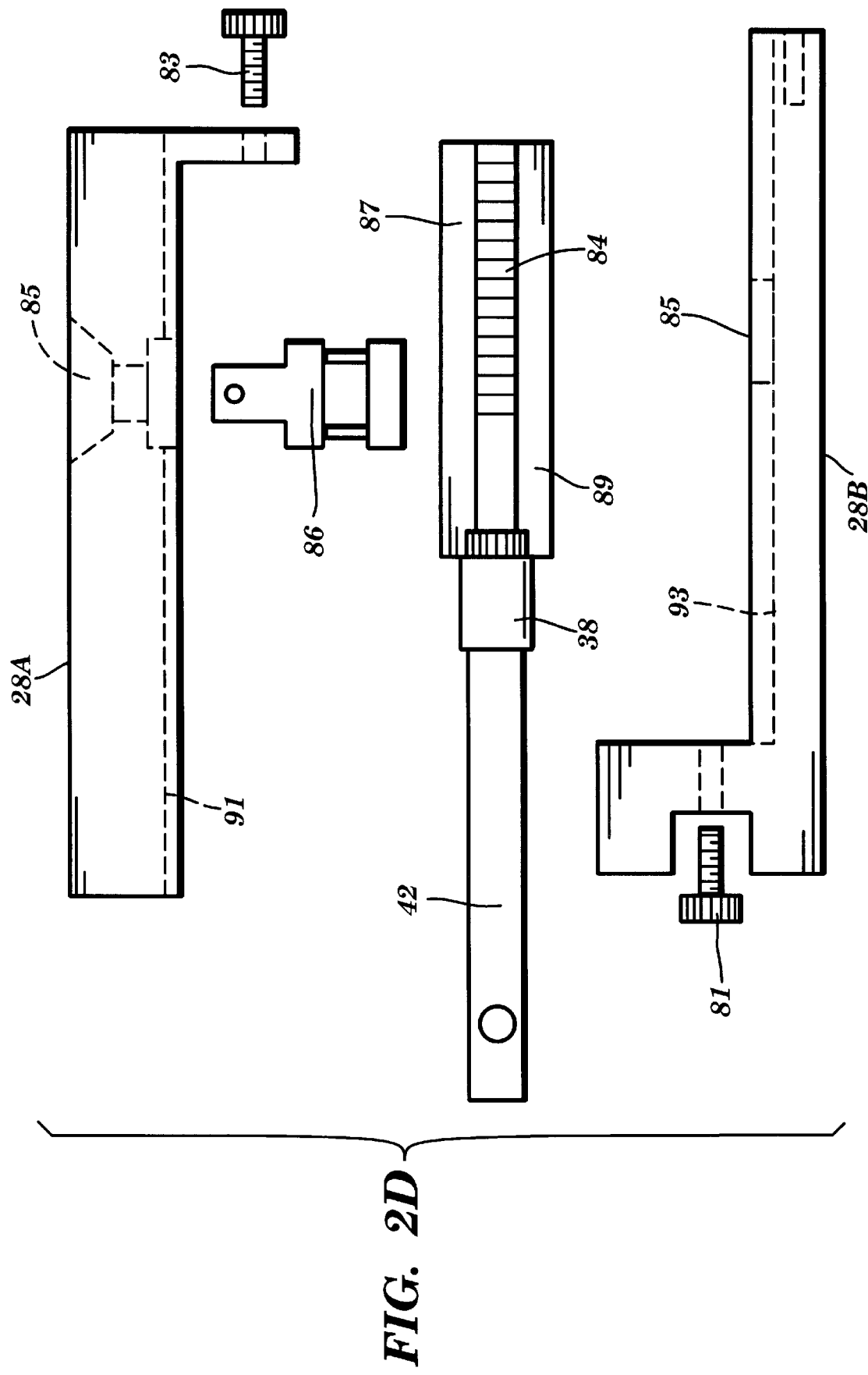
FIG. 2 is; a perspective view of the retractor endoscope.

Referring to FIG. 2c, handle 28 is formed from two sections 28a, 28b. To assemble the handle portion of retractor endoscope 10, translation frame 38 with rack 84 is sandwiched between sections 28a, 28b with the top and bottom edges 87, 89 of rack 84 slid into slots 91, 93 of sections 28a, 28b. Before placing section 28b over rack 84, pinion 86 is placed in opening 85 of section 28b. The assembly is held together with dismantling screw 83. Referring also to FIGS. 2 and 2A, U-frame 32 with lower blade mount 33 is then attached to the handle portion by sliding it over side rods 40, 42 and bolting it to handle 28 by screws 81, 81' (screw 81' not shown). Upper blade mount 39 is then positioned within U-frame 32 and the assembly is held together with screws 80, 82. Lower and upper blades 20, 22 are then slid into position in dovetails 24, 26 and locked via locking screws 60, 62.

Figure 3A:
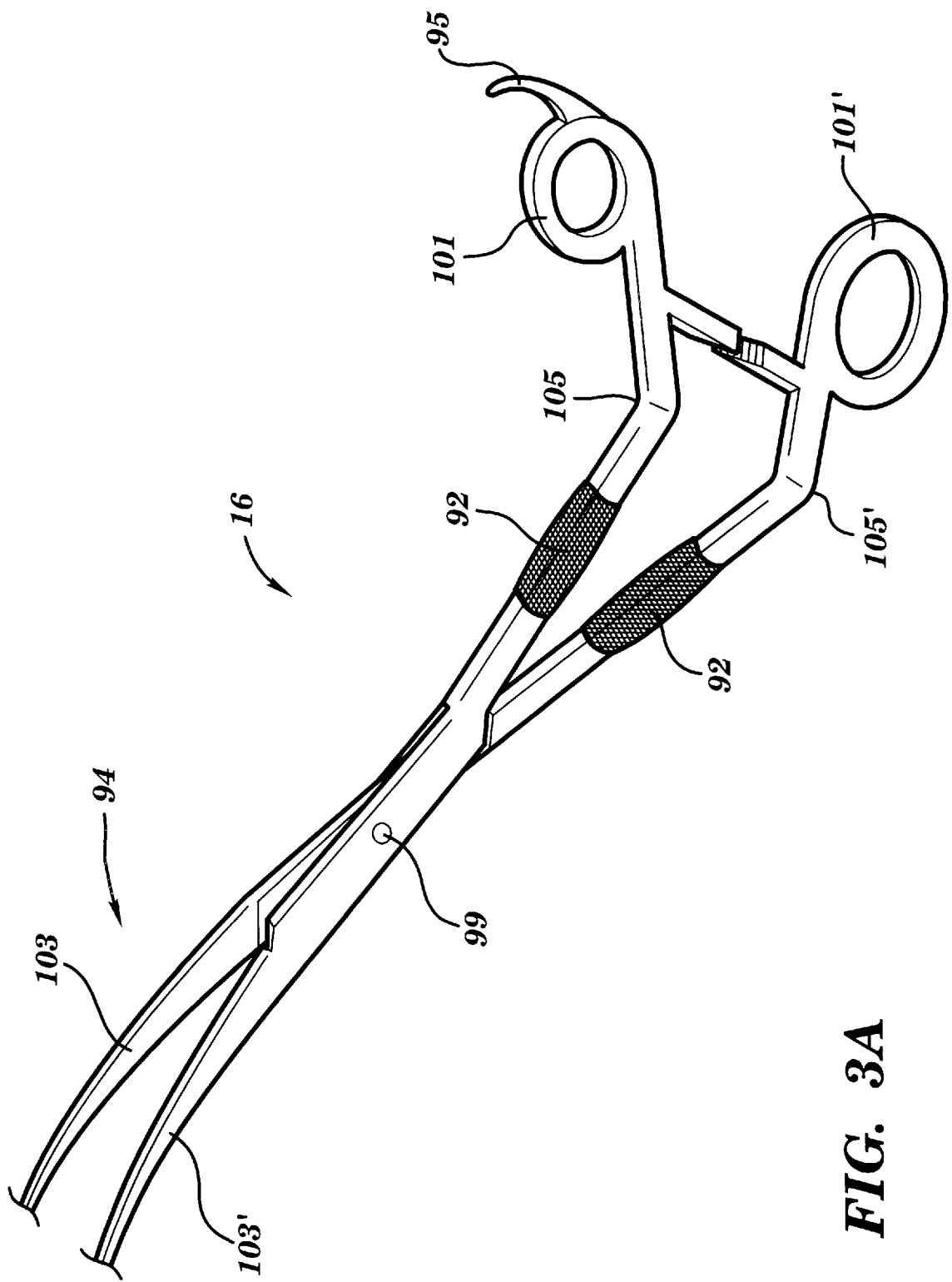
FIG. 3a is a perspective view of an alternative embodiment of an angled handle tool having a knurled finger pad shown positioned for right handed use.
Figure 3B:
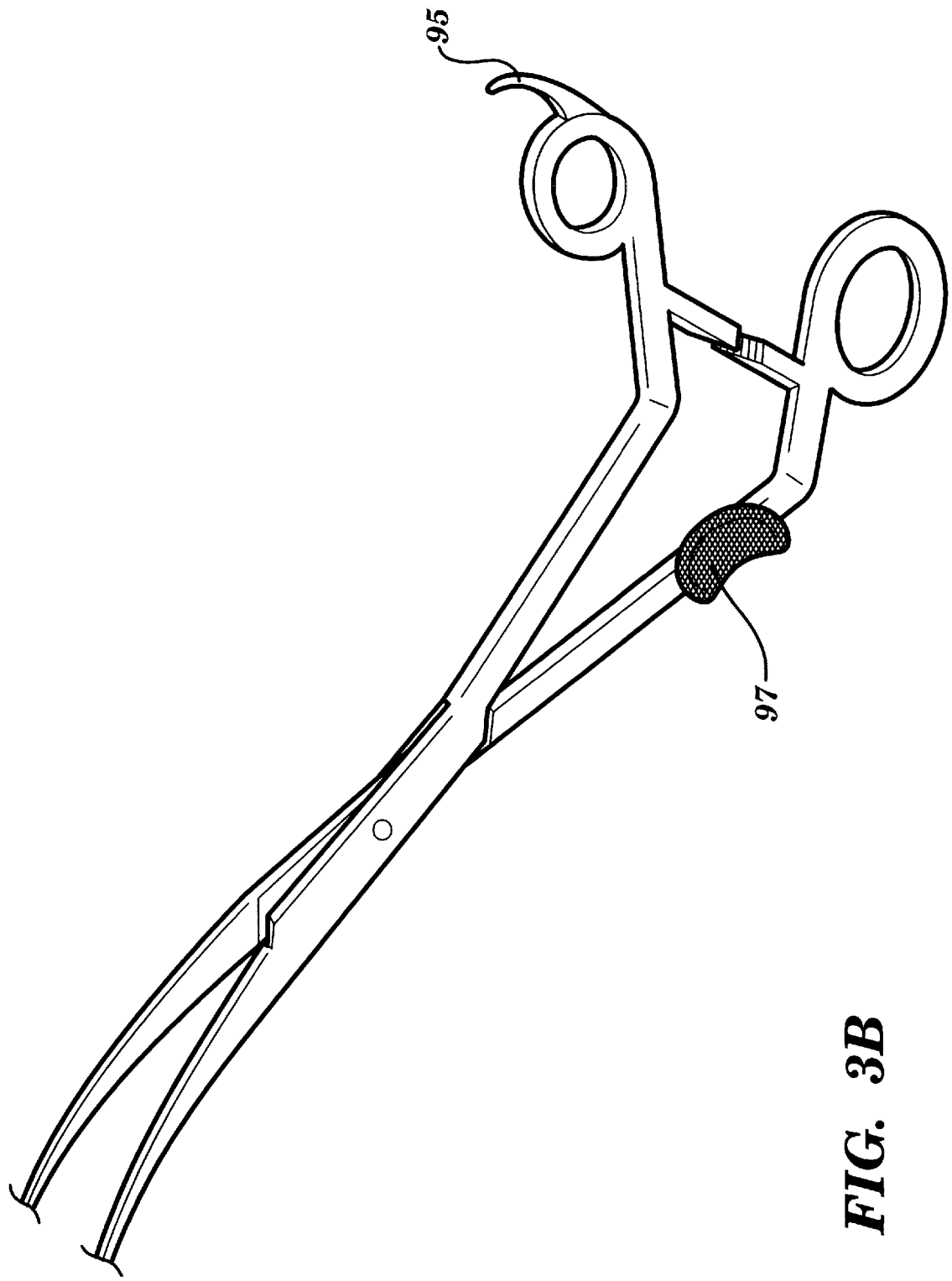
FIG. 3 is, a perspective view of an angled handled tool for use in combination with the apparatus.

Referring to FIG. 3, tool 16, used in combination with retractor endoscope 10, includes a proximal angled handle 90 (e.g., angled at 30, 45, or 60 degrees at bends 105, 105') which permits visualization of the surgical site during a procedure: by remaining clear of operating window 14 during use of tool 16. Proximal angled handle 90 also facilitates keeping the user's hand which is manipulating tool 16 from blocking operating window 14.

Proximal angled handle 90 includes two finger rings 101, 101'. Tool 16 has a distal working portion 94 for performing a surgical procedure which includes two working members 103, 103' and a single pivot joint 99 located between distal working portion 94 and proximal handle 90. Pivot joint 99 permits actuation of handle 90 by moving finger rings 101, 101' apart or together in a horizontal plane which results in working members 103, 103' moving apart or together in the same plane tilted at the angle of bends 105, 105'. Bends 105, 105' are located proximally of pivot joint 99; the distance between the proximal end of proximal handle 90 and bends 105, 105' is less than the distance between the distal end of working portion 94 and bend 105, 105'.

Tool 16 further includes knurled finger grips 92 located proximally of pivot point 99 and a spike finger support 95 located on finger ring 101 or 101', depending on left or right handed use. Finger grips 92 and spike finger support 95 facilitate precision handling of tool 16. Working portion 94 of tool 16 may be any suitable device for performing the desired procedure, e.g., forceps, clamps, needle holders. Referring to FIG. 3a, in another embodiment of tool 16, knurled finger grips 92 are replaced with knurled finger pad 97. Knurled finger pad 97 can be positioned for either left or right handed use.

Figure 4A:
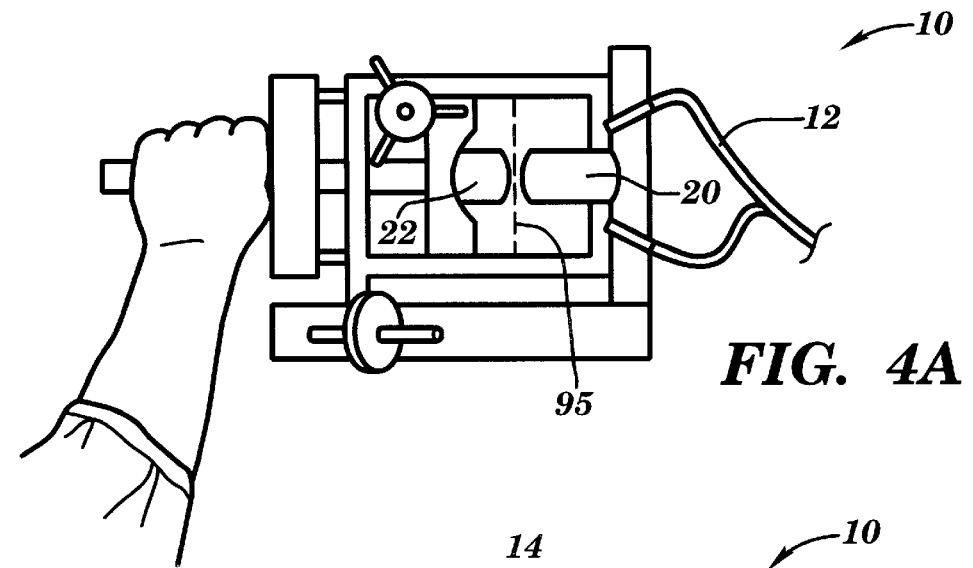
FIGS. 4–4b show the retractor endoscope in operation.
Figure 4B:
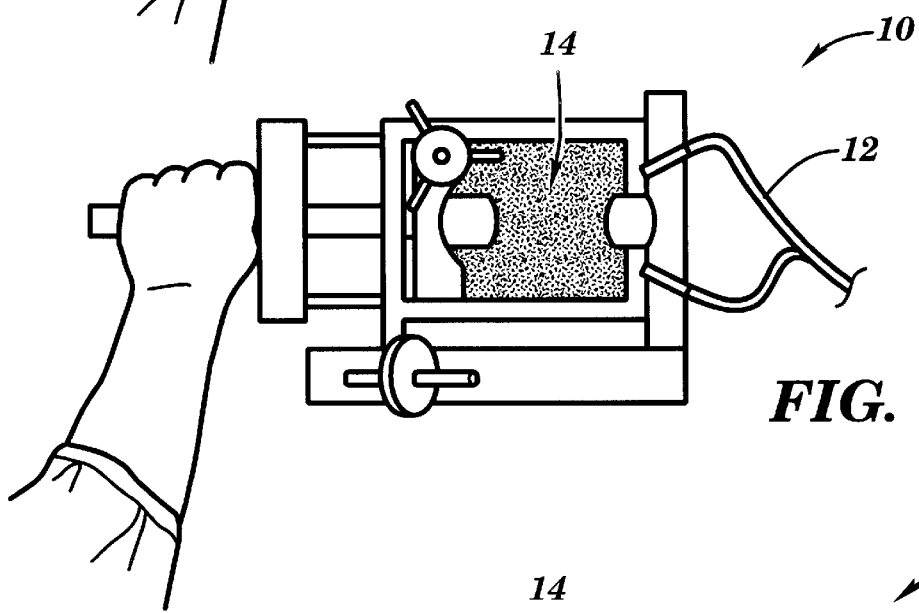
Figure 4C:
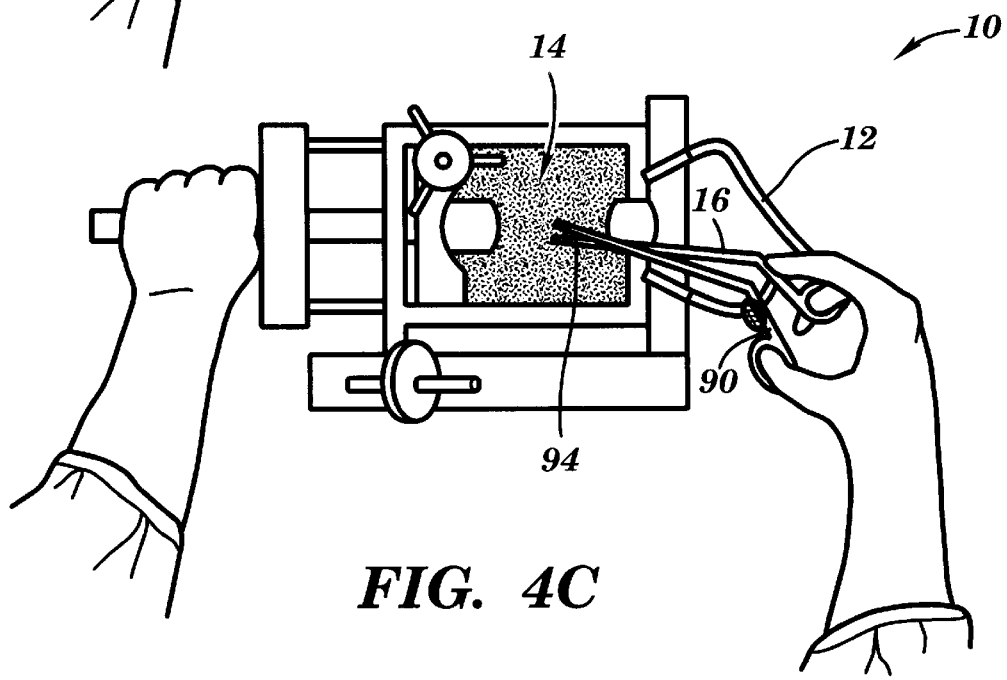

Referring to FIGS. 4–4b, in operation a short incision 95 (e.g., 3–6 times shorter than the incision made for the same procedure in conventional surgery) is made in the skin corresponding to the site of a surgical procedure. The use of a short incision results in more rapid healing, less wound surface, less bleeding and less pain than the standard sized incision used in conventional surgery. The incision is retracted by placing lower and upper blades 20, 22, angled with their free ends close together, into the incision. The desired sized operating window 14 is created by adjusting handle 28 and first and second assemblies 55, 51. The surgical site is illuminated with high intensity fiberoptic lighting 12.

Working portion 94 of tool 16 then enters the surgical site through operating window 14 while angled handle 90 remains removed from the surgical site. Surgery is then performed including manipulating working portion 94 of tool 16 through actuation of angled handle 90 while observing the surgical site through the operating window. This method facilitates performing surgical procedure while allowing illumination and binocular visualization of the operating site.

Figure 5:
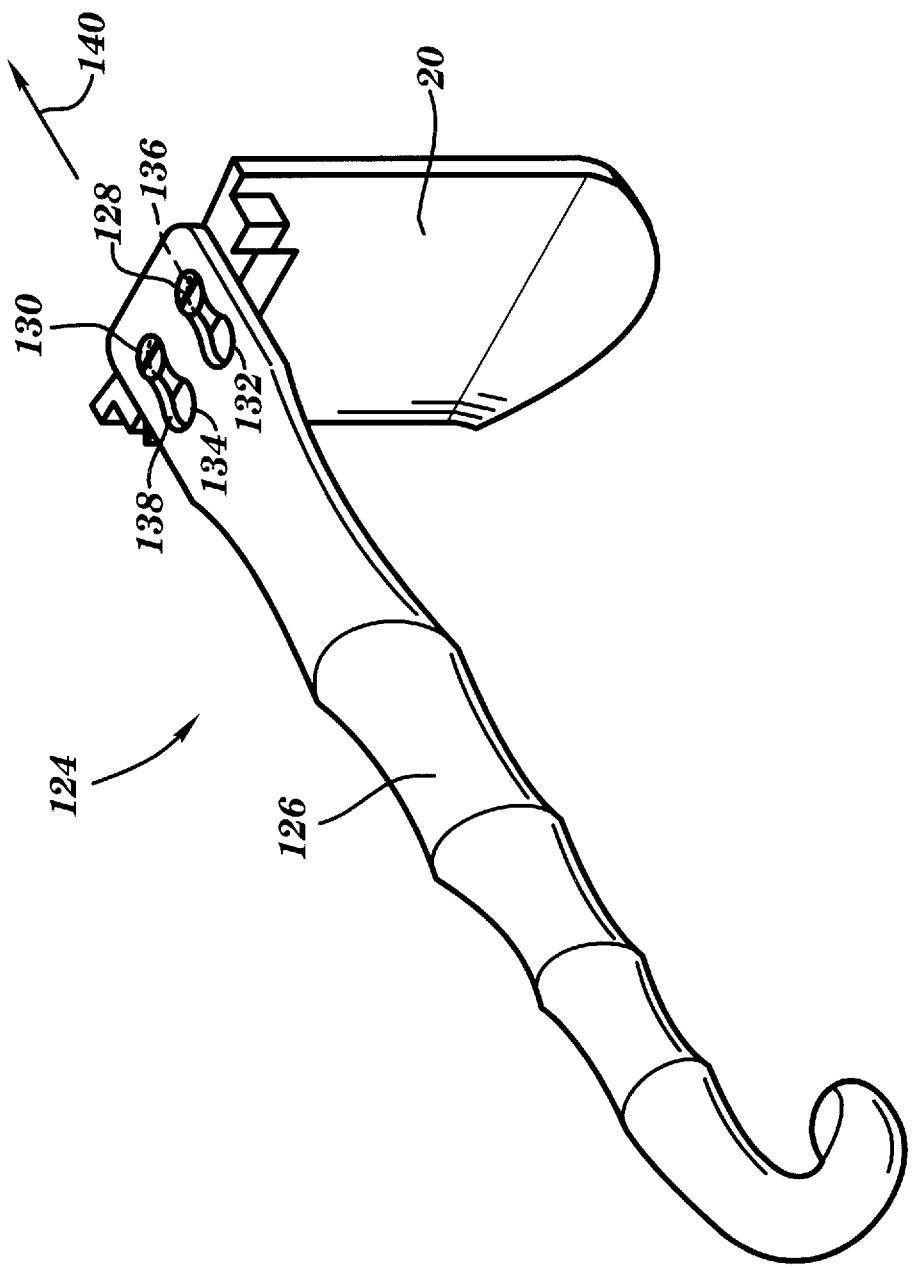
FIG. 5 is a perspective view of a hand retractor which may be used in combination with the retractor endoscope.

Referring to FIG. 5, in operation, a hand retractor may be employed to perform initial retraction and lighting of incision 95. Hand retractor 124 includes a handle 126 with a retractor blade (either lower blade 20 or upper blade 22, lower blade 20 shown) removably mounted thereto by screws 128, 130 through slots 132, 134. Slots 132, 134 have two circular sections, one section 136 having a smaller diameter than the diameter of the heads of screws 128, 130 so that the screw can be tightened for mounting, and another section 138 having a larger diameter than the screw head diameter so that the handle can be removed. Fiberoptic mounts 70 may replace one or both of screws 128, 130.

After initial retraction with hand retractor 124, screws 128, 130 are loosened, handle 126 is pushed in the direction of arrow 140 and removed leaving the retractor blade in place while retractor endoscope 10 is inserted. Retractor endoscope 10 includes only one of lower and upper blades 20, 22 leaving the other respective blade mount empty to accept the retractor blade which was left in place in incision 95 for attachment to retractor endoscope 10 during the insertion of retractor endoscope 10 into incision 95.

Figure 6:
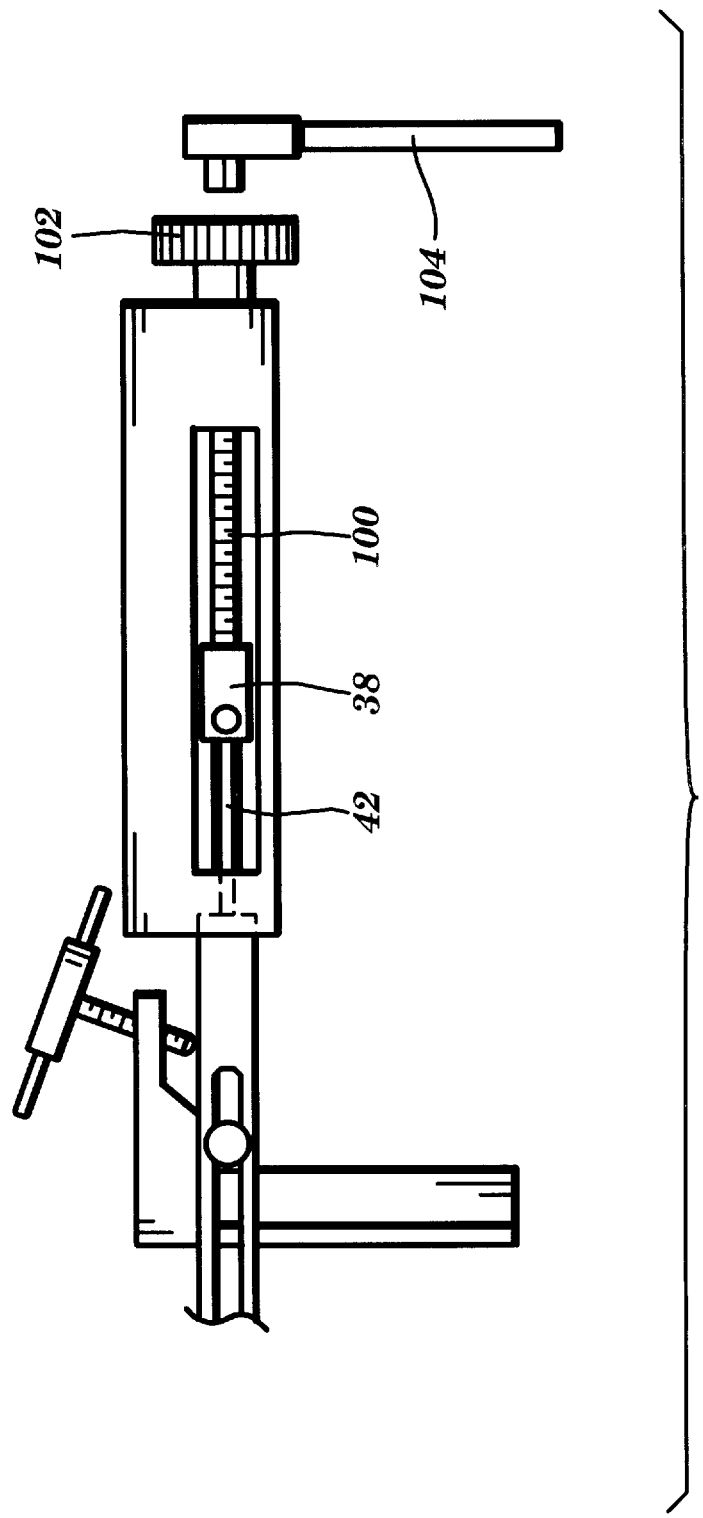
FIG. 6 is a side view of an alternative embodiment of the handle.

Various mechanisms may be employed to adjust the distance between lower and upper blade mounts 33, 39. Referring to FIG. 6, rack and pinion 84, 86 can be replaced with lead screw 100. Rotating knob 102 turns lead screw 100 translating frame 38. Torque wrench 104 can be used to apply additional torque to lead screw 100.

Figure 7:
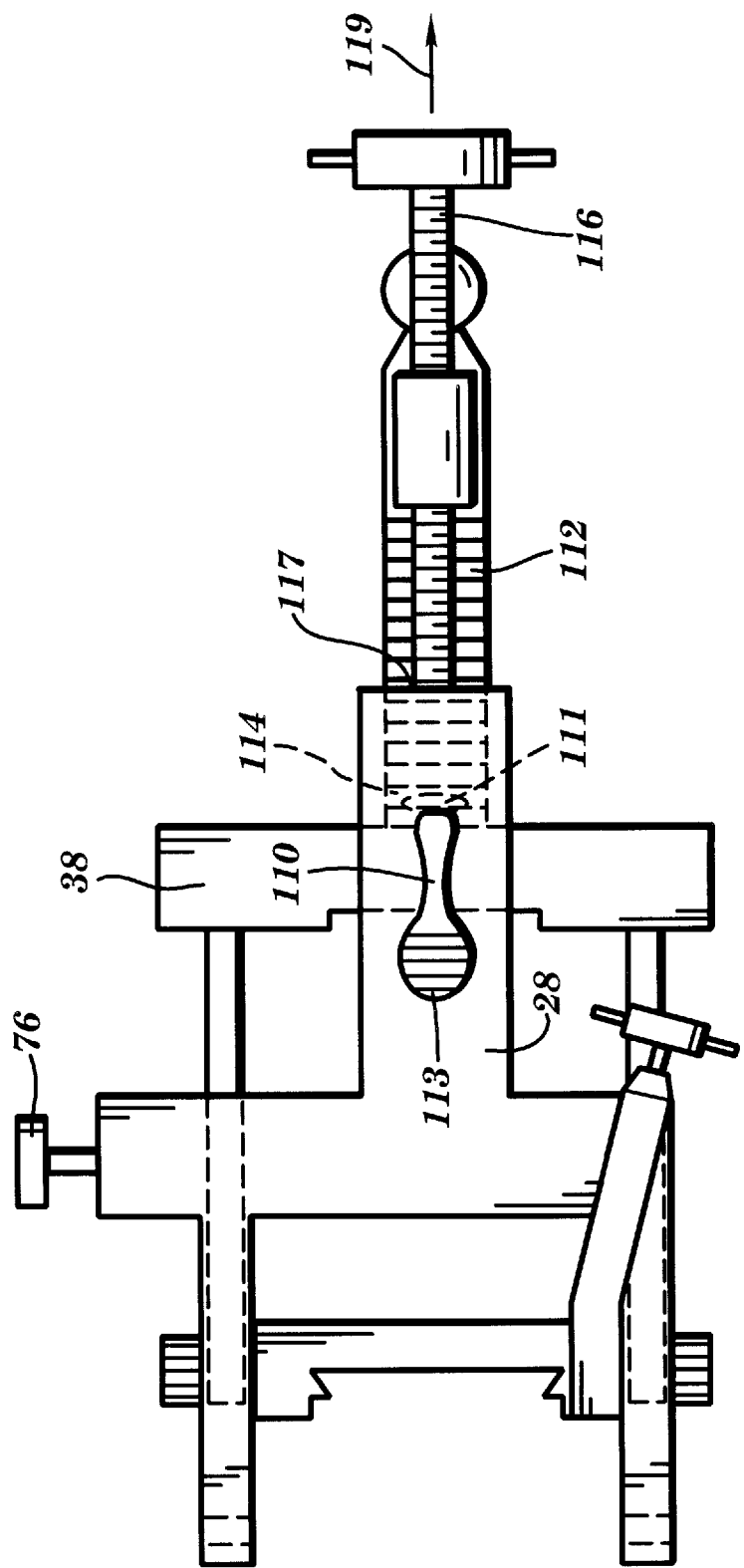
FIG. 7 is a top view of another alternative embodiment of the handle.

Referring to FIG. 7, rack and pinion 84, 86 can be replaced with a ratchet mechanism. Handle 28 includes finger pivot 110 with end 111 which locks into grooves 114 of ratchet 112, ratchet 112 being connected to translation frame 38. Frame 38 can be freely translated within handle 28 in the direction which moves lower and upper blade mounts 33, 39 further apart, but end 111 of finger pivot 110 falls into grooves 114 as the grooves pass by preventing free translation of frame 38 within handle 28 in the direction which moves lower and upper blade mounts 33, 39 closer together. This allows the position of lower and upper blade mounts 33, 39 to be maintained without having to apply continual load to retractor endoscope 10. In order to move lower and upper blade mounts 33, 39 closer together, end 111 must be moved out of groove 114 by pushing on pad 113 of finger pivot 110.

A biasing means, e.g., spring or spring steel, (not shown) may bet incorporated to bias finger pivot 110 in the position in which end 111 is engaged with groove 114. Screw 116 which is threadably mounted to ratchet 112 may be employed to aid in increasing the distance between lower and upper blade mounts 33, 39. With end 117 of screw 116 against handle 28, turning screw 116 causes ratchet 112 and thus translation frame 38 to move in the direction of arrow 119. Screw 116 must be backed off to allow lower and upper blade mounts 33, 39 to be moved closer together.

Figure 8:
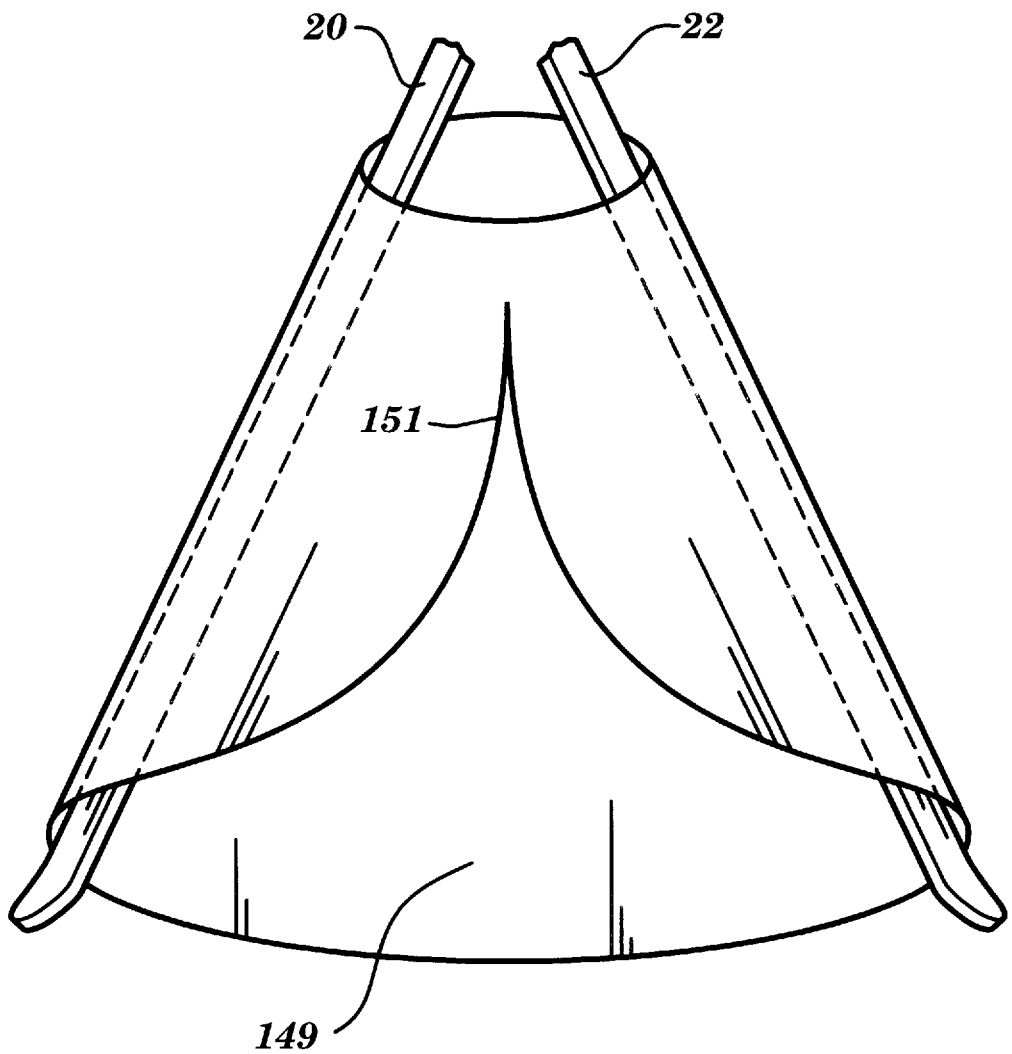
FIG. 8 is a side view showing a transparent plastic sleeve slid over the blades of the apparatus.

Removable blades 20, 22 may be sterilizable or disposable. Blade 20 may be different in length from blade 22. This is particularly useful in surgical procedures such as bladder neck surgery in which one of the blades would hit the pelvic bone if the blade were too long. In operation, the blades generally displace organs to create operating window 14. Referring to FIG. 8, in order to keep the organs out of the operating window, particularly in procedures such as bowel surgery, a retention device, e.g., a sleeve 149, can be placed around blades 20, 22. Sleeve 149 is sufficiently elastic to allow it to stretch and retract as blades 20, 22 are adjusted and may include a slit 151 facing away from an area containing organs to be retained, thus allowing access to a surgical area beyond slit 151. Alternatively, referring to FIG. 9, one or two side blades 142 may be utilized for this purpose.

Blades 20, 22 may include windows to enable viewing of the anatomy beyond the blades. The shape of blades 20, 22 may vary, e.g., non-rectangular, wider, narrower, shorter, longer. Blades 20, 22 are replaceable. This is particularly advantageous if, after initial insertion of retractor endoscope 10, it is found that one or both of the blades are of the wrong size.

An advantage of the current invention is that the surgeon can use his or her own two eyes to view the surgical site. Thus the surgeon has a three-dimensional direct image through a relatively short incision. Additionally, fine needle suturing is relatively easy and precise.

An additional advantage of the current system is that if operating window 14 is incorrectly positioned, the angle of viewing can be adjusted by tilting retractor endoscope 10 as a unit or by independently moving the blades, thus viewing a new area without making an additional incision.

Additionally, the current invention utilizes shorter incisions (e.g. 3–6 times shorter) than conventional surgery and provides three-dimensional direct viewing and direct access to the surgical site, facilitating shorter operating times. For example, in aorto-bifemoral bypass surgery, the incision made is a sixth of the size of the incision made in conventional surgery. In nephrectomy, laparoscopically the procedure takes 5 ½ to 6 hours, conventionally the procedure takes one hour with a 30 to 32 cm incision site, with the current invention the procedure takes one hour with an incision site of approximately 6 cm. Additionally, the surgeon can place his or her fingers into the surgical site and perform manual palpation.

Retractor endoscope 10 can be used in a wide variety of surgical procedures including vascular, cardiac, spinal, pulmonary, urology, trauma and abdominal surgery. During spinal fusion, access to the surgical site can be obtained through a mini-incision from the front of the body instead of from the back. For heart or lung surgery a rib does not have to be removed; rigid U-frame 32 must be able to support the load seen by retractor endoscope 10 while retracting and holding the ribs apart to allow access to the heart or lung.

Retractor endoscope 10 can be used in conjunction with operating room microscopes, videocameras, binocular magnifying loops and surgical lasers. Additionally, retractor endoscope 10, tool 16 and hand retractor 124 may be used in conjunction with a magnetic resonance imaging system provided they are constructed from nonmagnetic material, e.g., titanium.

Figure 9:
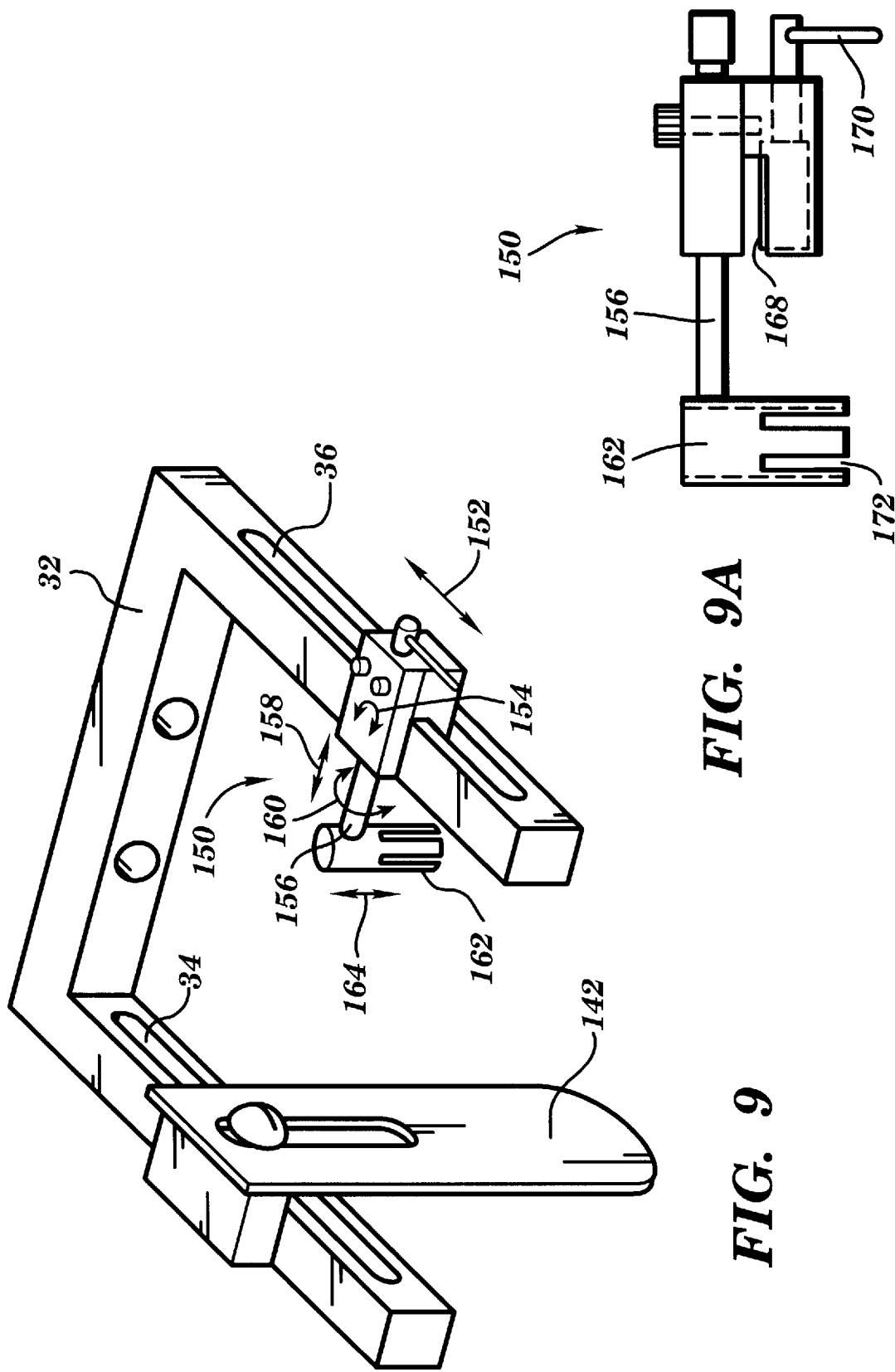
FIG. 9 is a perspective view of a microcamera mount and a slide blade attached to the apparatus.

Referring to FIGS. 9–9a, U-frame 32 includes an adjustable mount 150 for a video microcamera (not shown). Mount 150 is attached to U-frame 32 along either rigid frame slot 34 or 36 (shown in slot 36) such that mount 150 can slide along arrow 152 and rotate along arrow 154. Arm 156 of mount 150 can translate along arrow 158 and rotate along arrow 160. A microcamera holder 162 slidably holds the microcamera allowing the magnification of the microcamera to be adjusted by sliding the microcamera along arrow 164 within microcamera holder 162. Microcamera holder 162 may be fluted with slots 172. If necessary, microcamera holder 162 may contain a lens for use with the microcamera. Mount 150 can be locked in place against U-frame 32 by rotating a cam lock 168 using rod 170, thus preventing motion along arrows 152, 154, 158 and 160.

Other embodiments are within the following claims.

What is claimed is:

1. A method of less invasive, direct access endoscopic surgery within a surgical site, said surgery performed through an operating window created with an apparatus comprising a rigid frame capable of supporting applied loads required to perform retraction of an incision site, said rigid frame including a handle at one end, said handle having a handle slot therein, a lower blade mount rotatable connected to said rigid frame opposite said handle, rigid frame slots on either side of said rigid frame, and a translation frame slidably connected to said rigid frame through said handle slot and said rigid frame slots and including an upper blade mount connected thereto, said slidable connection constructed and arranged to allow said handle to translate said translation frame with respect to said rigid frame to adjust a distance between said lower blade mount and said upper blade mount, said handle constructed and arranged to prevent sliding of said translation frame along said slidable connection in at least one direction, said apparatus further including a lower blade and an upper blade, each blade having a free end and a supported end, mounted to said lower and upper blade mounts respectively, a first adjusting assembly functionally connected between said lower blade mount and said rigid frame for independently adjusting the angle of said lower blade mount without lateral displacement of said lower blade mount, and a second adjusting assembly connected between said upper blade mount and said rigid frame for independently adjusting the angle of said upper blade mount without lateral displacement of said upper blade mount, said first and second adjusting assemblies constructed and arranged to prevent rotation along said rotatable connections in at least one direction, wherein the size of said operating window is determined by the distance between said lower blade mount and said upper blade mount as set by the handle and by the angles of said lower and upper blades as set by said first and second adjusting assemblies, said method comprising:

creating a small incision in the skin corresponding to said surgical site;

retracting the incision by placing said apparatus, with said lower and upper blades angled such that the free ends of said lower and upper blades are close together, over said incision and inserting said lower and upper blades into the incision and adjusting said handle and said first and second adjusting assemblies to create the desired sized operating window; and performing surgery within the surgical site through said operating window.

2. The method of claim 1, wherein at least one of said lower blade and said upper blade includes at least one pivot mount for a high intensity fiberoptic, and wherein said method further comprises illuminating said surgical site with said high intensity fiberoptic.

3. The method of claim 1 wherein said apparatus further includes a manipulating tool having an angled handle wherein said angled handle is clear of the operating window during use of said tool to enable visualization of the surgical, and wherein said method further comprises the step of causing a working portion of said manipulating tool to enter said surgical site through said operating window while said angled handle remains removed from said surgical site, and wherein said step of performing surgery comprises manipulating the working portion of said manipulating tool within said surgical site, through actuation of said angled handle, while observing the surgical site through the operating window.

4. The method of claim 3 wherein said manipulating tool is selected from the group consisting of clamps, forceps, and needle holders.

5. The method of claim 1 further comprising tilting said apparatus to adjust the operating window.

6. An apparatus for creating an adjustable operating window for less invasive, direct access endoscopic surgery, said apparatus comprising:

a rigid frame capable of supporting applied loads required to perform retraction of an incision site, said rigid frame including a handle at one end;

a lower blade mount rotatably connected to said rigid frame opposite said handle;

a translation frame slidably connected to said rigid frame through a rigid frame slot on each side of said rigid frame, wherein said slidable connection is constructed and arranged to allow said handle to translate said translation frame with respect to said rigid frame and wherein said handle is constructed and arranged to prevent sliding of said translation frame along said slidable connection in at least one direction;

an upper blade mount rotatably connected to said translation frame, wherein a distance between said lower blade mount and said upper blade mount is adjusted by sliding said translation frame along said slidable connection;

a lower blade releasably attached to said lower blade mount;

an upper blade releasably attached to said upper blade mount;

a first adjusting assembly functionally connected between said lower blade mount and said rigid frame for independently adjusting the angle of said lower blade mount without lateral displacement of said lower blade mount; and a second adjusting assembly functionally connected between said upper blade mount and said rigid frame for independently adjusting the angle of said upper blade mount without lateral displacement of said upper blade mount, and wherein said first and second adjusting assemblies are constructed and arranged to prevent rotation along said rotatable connections in at least one direction, wherein the size of said operating window is determined by the distance between said upper and lower blade mounts as set by said handle, and by the angles of said upper and lower blades as set by said first and second adjusting assemblies.

7. The apparatus of claim 6, wherein the handle includes means for translating said translation frame, said translating means constructed and arranged to prevent sliding of said translation frame in at least one direction.

8. The apparatus of claim 7, wherein said translating means comprises a rack and pinion mechanism.

9. The apparatus of claim 7, wherein said translating means comprises a lead screw mechanism.

10. The apparatus of claim 9 further comprising a torque wrench removably connected to said lead screw mechanism for increasing the torque applied to said lead screw mechanism.

11. The apparatus of claim 7, wherein said translating means comprises a ratchet mechanism.

12. The apparatus of claim 6, wherein said handle includes a handle slot therein and wherein said translation frame is slidably connected to said rigid frame through said handle slot and said rigid frame slots.

13. The apparatus of claim 6, wherein at least one of said upper and said lower blades includes a pivot mount for a high intensity fiber optic.

14. The apparatus of claim 6 wherein at least one of said first and said second adjusting assemblies comprises an adjusting screw and bar assembly functionally connected between said upper or said lower blade mount and said rigid frame.

15. The apparatus of claim 6 wherein said rigid frame is attachable to a securing arm during surgery.

16. The apparatus of claim 6 further comprising a scale fixedly attached to said rigid frame for measuring the distance between said lower blade mount and said upper blade mount.

17. The apparatus of claim 16 wherein said scale is laser etched to said rigid frame.

18. The apparatus of claim 6 further comprising a microcamera mount connected to said rigid frame.

19. The apparatus of claim 18, wherein said microcamera mount is slidably and rotatably connected to said rigid frame in said rigid frame slot.

20. The apparatus of claim 19, wherein said microcamera mount further includes a cam lock for locking said mount in said rigid frame slot.

21. The apparatus of claim 19, wherein said microcamera mount further comprises a microcamera holder, the magnification of the microcamera being adjustable by sliding the microcamera within said microcamera holder when seated in said microcamera holder.

22. The apparatus of claim 6 further comprising a retention device for keeping body parts clear of said operating window.

23. The apparatus of claim 22 wherein said retention device comprises a sleeve.

24. The apparatus of claim 22 wherein said retention device comprises a side blade.

25. The apparatus of claim 6 formed from nonmagnetic material.

26. The apparatus of claim 25 wherein said nonmagnetic material is titanium.

27. The apparatus of claim 6 further comprising a tool for performing less invasive, direct access endoscopic surgery, said tool comprising:
 a distal working portion comprising two working members;
 a proximal handle disposed at a predetermined angle with respect to said distal working portion and including two finger rings; and
 a region between said distal working portion and said proximal handle including a single pivot joint between said two working members, said single pivot joint constructed and arranged so that actuation of said proximal handle by moving said finger rings apart or together in substantially a horizontal plane results in said working members moving apart or together in a working plane tilted at said predetermined angle from said horizontal plane.

28. The apparatus of claim 27 wherein said region between said distal working portion and said proximal handle of said tool further comprises a gripping zone.

29. The apparatus of claim 28 wherein said gripping zone comprises knurled finger grips.

30. The apparatus of claim 28 wherein said gripping zone comprises a knurled finger pad.

31. The apparatus of claim 27 wherein said tool further comprises a spike finger support integral with one of said finger rings.

32. The apparatus of claim 27 wherein said predetermined angle of said tool is located proximal of said pivot joint and the distance between the proximal end of said handle and said angle location is less than the distance between the distal end of said working portion and said angle location.

33. The apparatus of claim 6 further comprising a hand retractor for retracting an incision, said hand retractor comprising:
 a blade with at least two screws at a handle end, each screw having a head; and
 a handle with at least two slots at a blade end, said handle removably mounted to said blade by protrusion of said at least two screws through said at least two slots, each of said at least two slots including an area smaller than the corresponding screw head and an area larger than the corresponding screw head.

34. The apparatus of claim 33 wherein said hand retractor blade includes at least one pivot mount for a high intensity fiberoptic.

35. The apparatus of claim 6 wherein said lower blade and said upper blade differ in shape.

36. A method of less invasive, direct access endoscopic surgery performed within a surgical site through an operating window created with an apparatus comprised of a rigid frame capable of supporting applied loads during retraction of a surgical incision site, said rigid frame including a handle at one end, said handle having a handle slot therein, a lower blade mount rotatably connected to said rigid frame opposite said handle, rigid frame slots on either side of said rigid frame, and a translation frame slidably connected to said rigid frame through said handle slot and said rigid frame slots, said translation frame including an upper blade mount rotatably connected thereto, said slidable connection constructed and arranged to allow said handle to translate said translation frame, with respect to said rigid frame, to adjust a distance between said lower blade mount and said upper blade mount, said handle constructed and arranged to prevent sliding of said translation frame along said slidable connection in at least one direction, said apparatus further including a retractor blade mounted to one of said lower and upper blade mounts wherein the other of said lower and upper blade mounts is left empty, a first adjusting assembly functionally connected between said lower blade mount and said rigid frame for independently adjusting the angle of said lower blade mount without lateral displacement of said lower blade mount, and a second adjusting assembly connected between said upper blade mount and said rigid frame for independently adjusting the angle of said upper blade mount without lateral displacement of said upper blade mount, said first and second adjusting assemblies constructed and arranged to prevent rotation along said rotatable connections in at least one direction, wherein the size of said operating window is determined by the distance between said lower blade mount and said upper blade mount as set by the handle and by the angles of said lower and upper blade mounts as set by said first and second adjusting assemblies, said method of less invasive, direct access endoscopic surgery comprising the steps of:

creating a small incision in the skin corresponding to a surgical site;

retracting said incision with a hand retractor comprised of a retractor handle having a retractor blade removably attached thereto, by inserting said hand retractor blade into said incision;

removing said retractor handle from said hand retractor blade;

placing said apparatus over said incision;

inserting said apparatus retractor blade into said incision;

attaching said hand retractor blade to said empty blade mount on said apparatus;

adjusting said apparatus handle and said first and second adjusting assemblies to create the desired sized operating window; and performing surgery within said surgical site through said operating window.

37. The method of claim 36 wherein said hand retractor blade includes at least one pivot mount for a high intensity fiberoptic.

38. A method of less invasive, direct access endoscopic surgery performed with a retractor endoscope and a tool, said retractor endoscope having adjustable blades that can be positioned to create an operating window, said tool including a distal working portion comprising two working members, a proximal handle, angled at a predetermined angle with respect to said distal working portion, said proximal handle having two finger rings, and a region between said distal working portion and said proximal handle, said region including a single pivot joint, said single pivot joint constructed and arranged so that actuation of said proximal handle by moving said finger rings apart or together in substantially a horizontal plane results in said working members moving apart or together in a working plane tilted at said predetermined angle from said horizontal plane, said predetermined angle of said proximal handle enabling visualization through said operating window during use of said tool, said method comprising the steps of:

creating a short incision in the skin corresponding to a surgical site;

retracting the incision with said retractor endoscope to form an operating window and expose said surgical site;

pivoting said adjustable blades about an axis substantially parallel to or coplanar with said operating window, while the adjustable blades remain connected to the retractor endoscope, to increase access to the surgical site, without increasing the size of the operating window;

illuminating said operating window with high intensity fiberoptic lighting;

causing said working portion of said tool to enter said surgical site through said operating window while said proximal handle remains removed from said surgical site; and performing surgery within said surgical site wherein said surgery includes manipulating said working portion of said tool through actuation of said angled handle while observing said surgical site through said operating window.

39. An apparatus for less invasive, direct access endoscopic surgery within a surgical site, said surgery performed through an operating window, said apparatus comprising:

a rigid frame capable of supporting applied loads created during retraction of an incision, corresponding to said surgical site, said rigid frame including a handle at one end, said handle having a handle slot therein;

a lower blade mount rotatably connected to said rigid frame opposite said handle, wherein said lower blade mount rotates without lateral displacement thereof;

a rigid frame slot on either side of said rigid frame;

a translation frame slidably connected to said rigid frame through said handle slot and said rigid frame slots;

an upper blade mount rotatably connected to said translation frame, wherein said upper blade mount rotates without lateral displacement thereof, wherein said slidable connection is constructed and arranged to allow said handle to translate said translation frame, with respect to said rigid frame, to adjust the distance between said lower blade mount and said upper blade mount and wherein said handle is constructed and arranged to prevent sliding of said translation frame along said slidable connection in at least one direction;

a lower blade releasably mounted to said lower blade mount;

an upper blade releasably mounted to said upper blade mount;

at least one of said lower blade and said upper blade having at least one pivot mount for a high intensity fiberoptic;

a first adjusting assembly functionally connected between said lower blade mount and said rigid frame for independently adjusting the angle of rotation of said lower blade mount;

a second adjusting assembly functionally connected between said upper blade mount and said rigid frame for independently adjusting the angle of rotation of said upper blade mount, wherein said first and second adjusting assemblies are constructed and arranged to prevent rotation of said lower and upper blade mounts in at least one direction and wherein the size of said operating window is defined by the distance between said lower blade mount and said upper blade mount, as set by said handle, and by the angle of rotation of said lower blade mount and of said upper blade mount, as set by said first and second adjusting assemblies.

40. The apparatus of claim 39 wherein said slidable connection includes a rack and pinion mechanism to allow said handle to translate said translation frame.

41. The apparatus of claim 39 further comprising an adjustable microcamera mount for a video microcamera.

42. The apparatus of claim 41 wherein said adjustable microcamera mount is slidably and rotatably connected to said rigid frame in one of said rigid frame slots and wherein said adjustable microcamera mount includes a cam lock for locking said adjustable microcamera mount in said rigid frame slot.

43. The apparatus of claim 42 wherein said adjustable microcamera mount further includes a slidable and rotatable microcamera holder and wherein the magnification of said video microcamera, when seated in said microcamera holder, is adjusted by sliding said microcamera holder.

44. An apparatus for forming an operating window to perform less invasive, direct access endoscopic surgery comprising:

a rigid frame capable of supporting an applied load required to perform retraction of an incision site;

a translation frame slidably connected to said rigid frame wherein said rigid frame and said translation frame define said operating window;

an upper blade connected to said rigid frame and a lower blade connected to said translation frame;

adjustment means operatively engaged to said translation frame and rigid frame, said adjustment means being adapted to vary the load and size of said operating window;

at least one of said upper and lower blade being pivotable about an axis substantially parallel to or coplanar with said operating window while remaining connected to said rigid frame or said translation frame, respectively; and wherein pivoting said upper or lower blade about said axis, while connected to said rigid frame or said translation frame, respectively, increases access to a surgical site without increasing the size of the operating window.

45. An apparatus for forming an operating window to perform less invasive, direct access endoscopic surgery comprising:

a rigid frame capable of supporting an applied load required to perform retraction of an incision site;

a translation frame slidably connected to said rigid frame wherein said rigid frame and said translation frame define said operating window;

an upper blade mount connected to said rigid frame and a lower blade mount connected to said translation frame, said upper and lower blade mount being adapted to receive an upper and lower blade therein, respectively;

adjustment means operatively engaged to said translation frame and rigid frame, said adjustment means being adapted to vary the load and size of said operating window;

at least one or more of said upper and lower blade mounts being pivotable about an axis substantially parallel to or coplanar with said operating window while remaining connected to said rigid frame or said translation frame, respectively; and wherein pivoting said upper or lower blade mount about said axis, while connected to said rigid frame or said translation frame, respectively, increases access to a surgical site without increasing the size of the operating window.

46. The apparatus of claim 45 further comprising:

a lower blade releasably attached to said lower blade mount;

an upper blade releasably attached to said upper blade mount, wherein said lower blade and said upper blade rotate concurrently with said lower blade mount and said upper blade mount respectively, and wherein the size of said operating window is further defined boy the rotation of said lower blade and said upper blade.

47. The apparatus of claim 46, further comprising at least one pivot mount for a high intensity fiber optic line, wherein said pivot mount allows said fiber optic line disposed therein to illuminate the surgical site through said operating window.

48. The apparatus of claim 47 wherein said at least one pivot mount is located on at least one of said lower blade and said upper blade.

* * * * *

UNITED STATES PATENT AND TRADEMARK OFFICE
CERTIFICATE OF CORRECTION

PATENT NO. : 5,813,978
DATED : Sept. 29, 1998
INVENTOR(S) : Jako

It is certified that error appears in the above-identified patent and that said Letters Patent is hereby corrected as shown below:

Column 16, line 27  Delete "boy" and insert --by--

Signed and Sealed this

Fourth Day of May, 1999

Attest:

Q. TODD DICKINSON

Attesting Officer  Acting Commissioner of Patents and Trademarks